(12) United States Patent
Boutoussov et al.

(10) Patent No.: US 8,821,483 B2
(45) Date of Patent: Sep. 2, 2014

(54) INITIATION SEQUENCES FOR RAMPING-UP PULSE POWER IN A MEDICAL LASER HAVING HIGH-INTENSITY LEADING SUBPULSES

(75) Inventors: Dmitri Boutoussov, Dana Point, CA (US); Ronald D. McKee, Lake Forest, CA (US)

(73) Assignee: Biolase, Inc., Irvine, CA (US)

( * ) Notice: Subject to any disclaimer, the term of this patent is extended or adjusted under 35 U.S.C. 154(b) by 0 days.

(21) Appl. No.: 13/283,458

(22) Filed: Oct. 27, 2011

(65) Prior Publication Data

US 2012/0116371 A1    May 10, 2012

Related U.S. Application Data

(60) Provisional application No. 61/410,111, filed on Nov. 4, 2010.

(51) Int. Cl.
*A61B 18/20* (2006.01)

(52) U.S. Cl.
USPC ............................................. 606/11; 606/15

(58) Field of Classification Search
USPC .................................... 606/1–19; 607/88–94
See application file for complete search history.

(56) References Cited

U.S. PATENT DOCUMENTS

| | | | | |
|---|---|---|---|---|
| 4,541,055 A | * | 9/1985 | Wolfe et al. ..................... 700/166 |
| 4,675,872 A | * | 6/1987 | Popek et al. ..................... 372/10 |
| 4,926,429 A | * | 5/1990 | Chung ............................ 372/32 |
| 5,881,079 A | * | 3/1999 | Doerr et al. ..................... 372/20 |
| 5,999,549 A | * | 12/1999 | Freitag et al. .............. 372/38.09 |
| 6,115,397 A | * | 9/2000 | Heritier et al. ................... 372/33 |
| 6,144,684 A | * | 11/2000 | McMinn et al. ........... 372/50.12 |
| 6,455,807 B1 | | 9/2002 | Scott |
| 6,607,524 B1 | * | 8/2003 | LaBudde et al. ................ 606/10 |
| 6,711,189 B1 | * | 3/2004 | Gilliland et al. ........... 372/38.02 |
| 6,870,863 B1 | * | 3/2005 | Butler et al. .............. 372/29.014 |
| 6,933,475 B2 | * | 8/2005 | Lano et al. ..................... 219/494 |
| 6,947,456 B2 | * | 9/2005 | Chin et al. ................. 372/38.02 |
| 6,998,567 B2 | * | 2/2006 | Yeik ......................... 219/121.61 |
| 7,031,352 B2 | * | 4/2006 | Palmer et al. ..................... 372/9 |
| 7,106,036 B1 | * | 9/2006 | Collins ......................... 323/282 |
| 7,280,575 B2 | * | 10/2007 | Moran et al. ............... 372/38.02 |
| 7,313,155 B1 | * | 12/2007 | Mu et al. ......................... 372/10 |

(Continued)

FOREIGN PATENT DOCUMENTS

| EP | 0425309 | 5/1991 |
|---|---|---|
| EP | 0425309 B1 | 2/1997 |

OTHER PUBLICATIONS

International Preliminary Report on Patentability mailed on Oct. 18, 2012 for corresponding PCT patent application No. PCT/US11/58167 filed on Oct. 27, 2011.

(Continued)

*Primary Examiner* — Gary Jackson
*Assistant Examiner* — Manolis Pahakis
(74) *Attorney, Agent, or Firm* — Jones Day

(57) ABSTRACT

A gradual ramp-up of output power in a medical laser prevents rapid temperature rise at a fiber tip of a laser handpiece when residual contamination from a prior medical procedure remains on the fiber tip after an extended cooling period. The gradual ramp-up eliminates effects of an acoustic shock wave resulting from the rapid temperature rise to prevent damage to fiber and optical components in the laser device.

16 Claims, 4 Drawing Sheets

(56) References Cited

U.S. PATENT DOCUMENTS

| | | | |
|---|---|---|---|
| 7,395,003 B2* | 7/2008 | Dan | 399/70 |
| 8,297,248 B2* | 10/2012 | Martin et al. | 123/143 B |
| 8,320,424 B2* | 11/2012 | Bolt et al. | 372/55 |
| 8,361,058 B2* | 1/2013 | Abe et al. | 606/4 |
| 2003/0127439 A1* | 7/2003 | Wee et al. | 219/121.73 |
| 2006/0016790 A1 | 1/2006 | Yeik | |
| 2006/0197756 A1* | 9/2006 | Sun | 345/179 |
| 2006/0203862 A1* | 9/2006 | Bonen et al. | 372/34 |
| 2007/0000501 A1* | 1/2007 | Wert et al. | 128/898 |
| 2008/0095201 A1* | 4/2008 | Mu et al. | 372/10 |
| 2008/0099187 A1 | 5/2008 | Rini et al. | |
| 2009/0034071 A1* | 2/2009 | Jennings et al. | 359/494 |
| 2009/0130622 A1* | 5/2009 | Bollinger et al. | 433/29 |
| 2011/0018854 A1* | 1/2011 | Barclay et al. | 345/211 |
| 2011/0106068 A1* | 5/2011 | Horvath et al. | 606/11 |
| 2011/0257640 A1* | 10/2011 | Choye et al. | 606/9 |

OTHER PUBLICATIONS

International Search Report and Written Opinion, PCT/US2011/058167, Jan. 31, 2012.

Notice of Preliminary Rejection dated Feb. 24, 2014 from related/corresponding Korean Patent Appl. No. 10-2013-7014224, filed Jun. 3, 2013.

\* cited by examiner

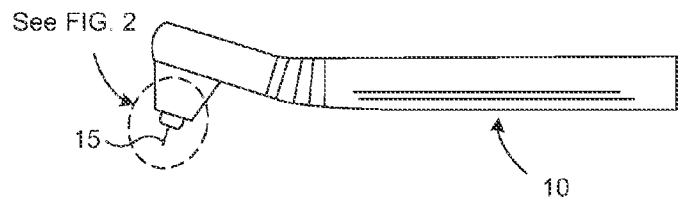
FIG. 1 (Prior Art)
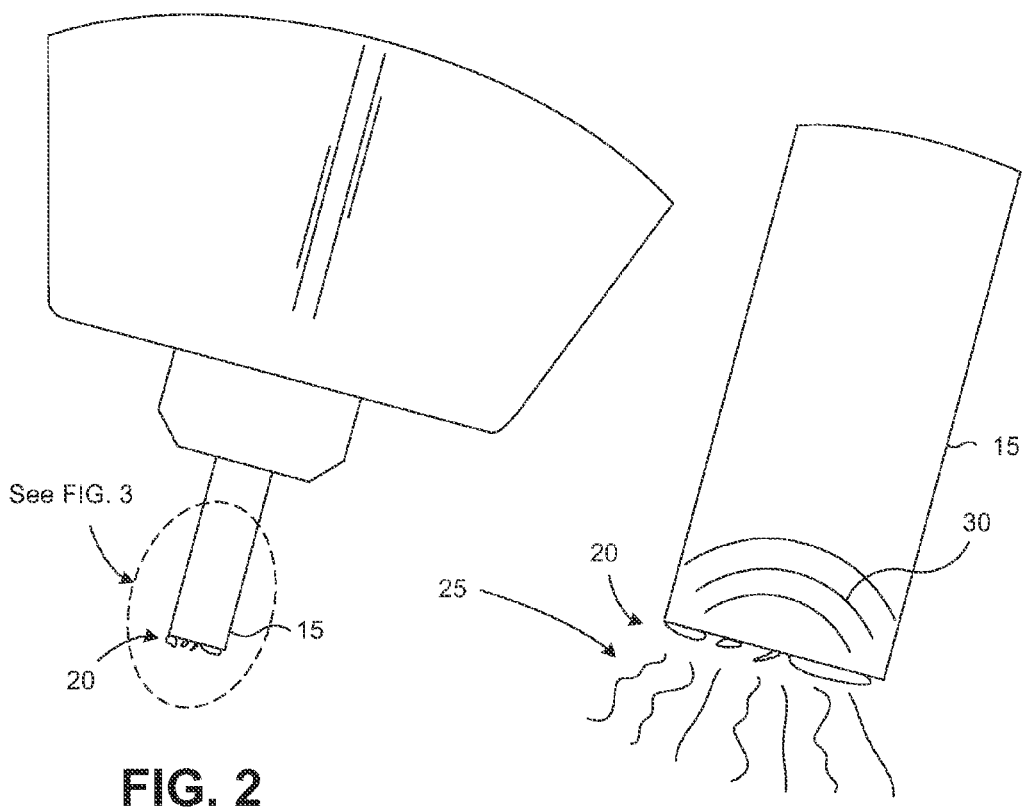
FIG. 2 (Prior Art)
FIG. 3 (Prior Art)

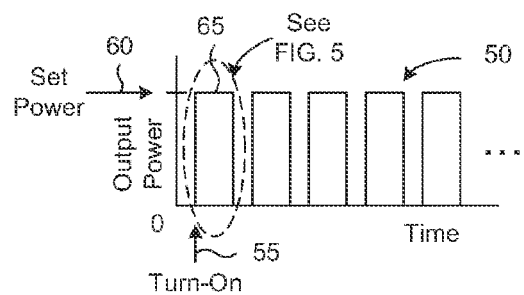
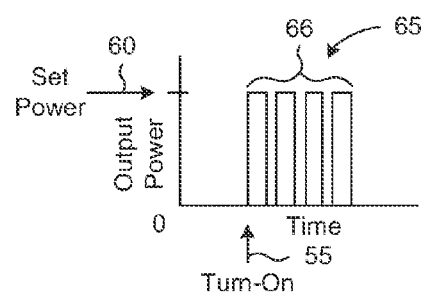
FIG. 4
(Prior Art)
FIG. 5
(Prior Art)
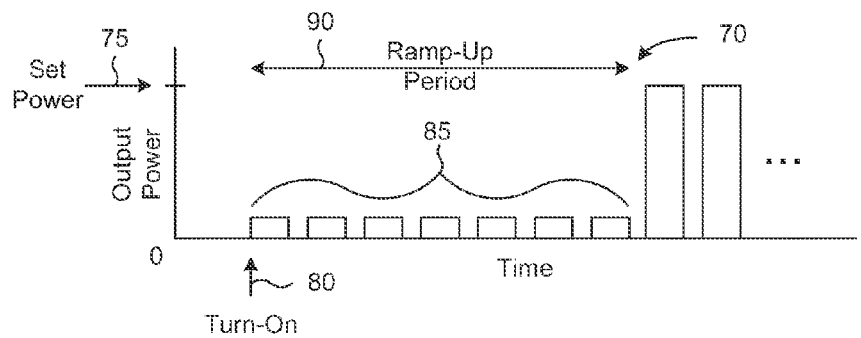
FIG. 6
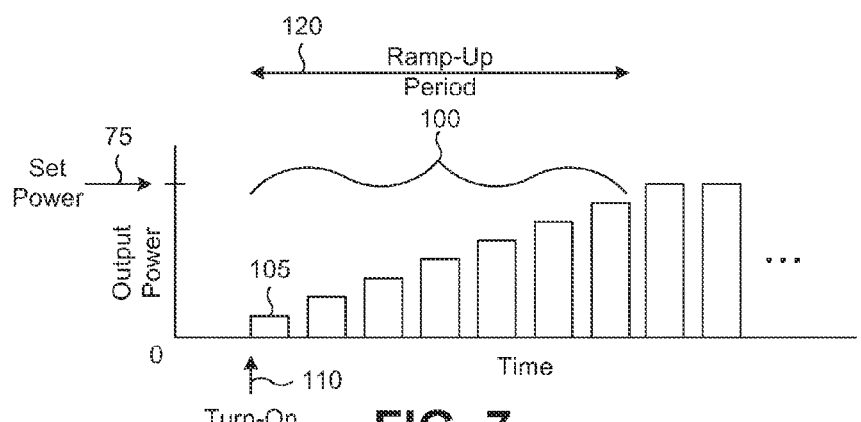
FIG. 7

INITIATION SEQUENCES FOR RAMPING-UP PULSE POWER IN A MEDICAL LASER HAVING HIGH-INTENSITY LEADING SUBPULSES

CROSS-REFERENCE TO RELATED APPLICATIONS

This application claims the benefit of Prov. App. 61/410,111, filed Nov. 4, 2010, the entire contents of which are hereby incorporated by reference.

BACKGROUND OF THE INVENTION

1. Field of the Invention

The present invention relates generally to medical lasers and, more particularly, to methods of preventing damage to medical lasers during startup.

2. Description of Related Art

Medical lasers find application in surgical and dental procedures. Laser power transmitted from a fiber tip can be used to treat (e.g., cut) biologic tissue such as skin, bone, dental tissue and the like. Various kinds of contamination of the fiber output can occur during this process. Water, blood, bits of tissue and even dust may accumulate on the fiber tip during use. Typically these impurities are burned off by action of the laser.

As one example, FIG. 1 illustrates a dental handpiece 10 that receives laser power from a laser module disposed in a laser housing and connected to the handpiece by a fiber optic waveguide (the laser module, laser housing and fiber optic waveguide are not shown in FIG. 1) that terminates in a fiber tip 15 that can emit laser energy to perform medical treatment. A more detailed view of the filter tip portion of the handpiece of FIG. 1 is illustrated in FIG. 2. After an extended period of non-use, particles of debris 20 that collect on the surface of the fiber 15, debris normally burned off by laser energy emitted from the fiber, may adhere to the fiber.

After such a period of non-use, suddenly transmitting a high level of laser power, corresponding, for example, to the opening of a shutter to generate a pulse of laser power, can cause the debris to rapidly and undesirably absorb a large amount of energy that can result in a rapid rise in temperature of the debris and the fiber tip. As illustrated in FIG. 3, this rapid temperature rise can trigger a sudden burst of heat and/or smoke 25 resulting from sudden burning of the debris 20 and can generate one or more acoustic shock waves 30 that can propagate along the fiber 15 toward the components of the handpiece 10 and into the laser housing and laser module with the potential that these components can be damaged.

A need exists in the prior art to ameliorate the effect of initial startup of a laser treatment device after an extended cooling-off period.

SUMMARY OF THE INVENTION

The present invention addresses this need by providing a medical laser that generates a startup sequence of pulses of electromagnetic energy, the startup sequence comprising an initial sequence having at least one pulse, the at least one pulse having a startup power level that is less than a set power level. An embodiment of the invention herein disclosed includes an initial sequence comprising a plurality of pulses including a first pulse and at least one other pulse, each pulse having a power level less than the set power level.

An implementation of the present invention comprises a method of activating a medical laser, the method comprising detecting a turn-on event and generating a ramp-up sequence. The generating may be performed in response to the turn-on event. According to another implantation, the generating is performed when a turn-off timer has expired.

Another embodiment of the present invention comprises a controller for a medical laser that includes a processor adapted to execute software instructions, working memory adapted to intercommunicate with the processor, and non-volatile memory adapted to store data. The controller may further include software modules, which may be stored in the non-volatile memory, the software modules comprising software instructions to cause the processor to perform turn-on detection, turn-off detection and sequence generation.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE FIGURES

FIG. 1 is a diagram of a prior-art dental handpiece;

FIG. 2 is a diagram showing a close-up view of a fiber that emits electromagnetic energy in the prior-art handpiece of FIG, 1;

FIG. 3 is a diagram showing further detail of the fiber of FIG. 2;

FIG. 4 is a chart illustrating a prior-art startup sequence for a medical laser;

FIG. 5 is a chart showing further detail of one pulse in the startup sequence of FIG. 4;

FIG. 6 is a chart illustrating one embodiment of a startup sequence for a medical laser according to the present invention;

FIG. 7 is a chart illustrating another embodiment of a startup sequence for a medical laser according to the present invention;

DETAILED DESCRIPTION OF THE PRESENTLY PREFERRED EMBODIMENTS

Figure 8:
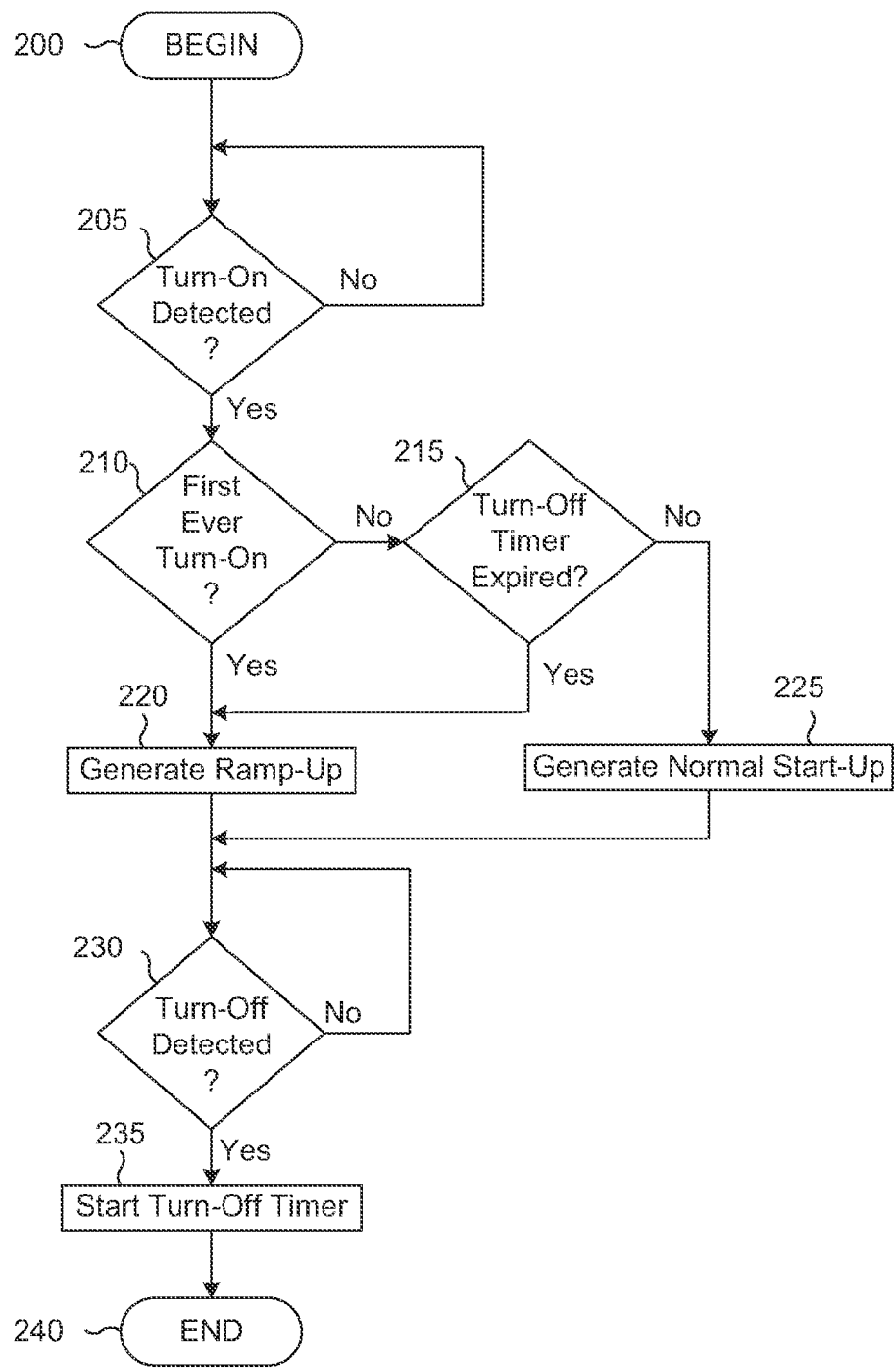
FIG. 8 is a flow diagram of a method of generating startup sequences in a medical laser.

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various laser operating techniques that are conventionally used in the art, and only so much of the commonly process steps are included herein as are necessary to provide an understanding of the present invention. The present invention has applicability in the field of laser devices in general. For illustrative purposes, however, the following description pertains to a medical laser and a related method of operation.

Referring again to the drawings, the chart portrayed in FIG. 4 illustrates an initial output for a prior-art medical laser. The typical output from such a device comprises a sequence of laser pulses 50 commencing during a turn-on time 55 at a set power level 60, which set power level 60 may correspond to a treatment power level. According to the prior-art device described, each pulse (e.g., a first pulse 65) of the sequence of laser pulses 50 comprises a sequence of subpulses 66 as illustrated in FIG. 5, the subpulses 66 not being depicted or distinguishable at the scale of FIG. 4. As already described, this method of startup for the medical laser can result in damage to the medical laser device.

FIG. 6 illustrates an initial output from a medical laser operated according to the present invention. The output comprises a sequence 70 of laser pulses having a set power level 75, the sequence 70 beginning at a turn-on instant 80 with a startup sequence 85 that is generated at a power level less than (e.g., ¹⁄₁₀) the set power level 75 during a ramp-up period 90. Each pulse in the startup sequence 85 after the initial pulse (i.e., the first pulse that commences at or about the turn-on time 80) may have a power level that is about the same as, or no greater than, the power level of the previous pulse in the sequence. A duration of the ramp-up period 90 illustrated in FIG. 6 may be about 1 second, but may be longer or shorter (e.g., may range from about 0.1 second to about 10 seconds) in some embodiments. It should be understood that each of the pulses illustrated in FIG. 6 might be implemented as a sequence of subpulses in a manner similar to that described herein with reference to FIGS. 4 and 5.

An alternative implementation of the present invention generates a startup output sequence 100 as illustrated in FIG. 7. An initial pulse 105 of the startup sequence commences at, during or about a turn-on time 110 at a relatively low power level. This relatively low power level may be, for example, about ¹⁄₁₀ of that of a set power level 75, which may correspond to a treatment power level. Subsequent pulses in the startup sequence each may have a power level that is about the same as or greater than the power level of the previous pulse in the sequence during a ramp-up period 120.

Additional implementations of the present invention will occur to one skilled in the art. For example, because each of the pulses in FIGS. 6 and 7 may comprise a sequence of subpulses (cf. FIG. 5), a startup sequence (e.g., ramp-up sequence) may comprise a sequence of subpulses each having a reduced power level, as illustrated in FIG. 6, or the ramp-up sequence may comprise a sequence of subpulses that begins, for example, at a turn-on time 110 (FIG. 7) and gradually increases in level with time beginning at a relatively low power level and ending at or below a set power level. Pulses in the startup sequence may have power levels in any combination, permutation or slight modification of those shown in FIGS. 6 and 7, such as, for example, the pulses having power levels corresponding to averages of those shown in the two charts whereby for instance in one implementation each successive pulse has a power level that is about the same as or greater than the power level of the previous pulse in the sequence during the ramp-up period. In another implementation one or more, or a majority of, or less than half of, the successive pulses can have a power level that is about the same as or greater than the power level of the previous pulse in the sequence during the ramp-up period.

In embodiments of the present invention corresponding to FIGS. 6 and 7, one or more of an initial pulse, a second pulse, or alternatively, the first three, four, five, six or more pulses in a startup sequence (e.g., startup sequence 85 in FIG. 6) is/are generated to be relatively low, e.g., ¹⁄₁₀ of one or more of the set power, which may be a power that would be generated by a medical laser device that had not cooled off (cf. FIG. 4). In a similar manner, startup sequences in other embodiments may comprise one or more of an initial subpulse, a second subpulse, or alternatively, the first three, four, five, six or more subpulses generated at a relative low power level relative to a set (e.g., treatment) power level that would occur if the device had not cooled off.

The present invention may, further, comprise a method of controlling an output power level of a medical laser. An implementation of the method is illustrated as a flow diagram in FIG. 8. The implementation, which may begin at step 200, waits at step 205 until a turn-on condition is detected. Such a turn-on condition (e.g., event) typically is detected in response to an operator activating a control on, for example, a handpiece, a foot pedal or the like. When the turn-on event is detected, a decision is made at step 210 as to whether this turn-on event is a first-ever turn-on event. A first-ever turn-on event may correspond to, for example, the turn-on of a new out-of-the-box device that has never been operated before or, as another example, the turn-on of a device that has been out of service due to maintenance, change of batteries, or the like. If at step 210 detection of a first-ever turn-on event occurs, then a ramp-up (e.g., startup) sequence of laser power output is generated as described supra with reference to FIGS. 6 and 7.

If, at step 210, the turn-on event is determined not to be a first-ever one, then a test is performed at step 215 to determine whether a turn-off timer has expired. A turn-off timer may be a device that starts when operation of a medical laser ceases (e.g., turns off) and then counts time until a set limit is reached. If the turn-off timer count reaches the set limit, then the timer may be said to have expired. The set limit may be controlled by an operator, according to one embodiment. Typical values for a set limit may be 30 seconds, 1 minute, 5 minutes or 10 or more minutes. If the turn-off timer has not expired (a possible indication that the laser has not cooled off or substantially cooled), then a normal startup sequence such as that illustrated in FIG. 4 may be generated at step 225.

Subsequent to the commencement of either the ramp-up sequence (step 220) or the normal startup sequence (step 225), a wait loop including step 230 may cycle until the laser has been turned off. When turn-off is detected at step 230, the turn-off timer may be started at step 235, after which the implementation of the method may terminate at step 240.

Figure 9:
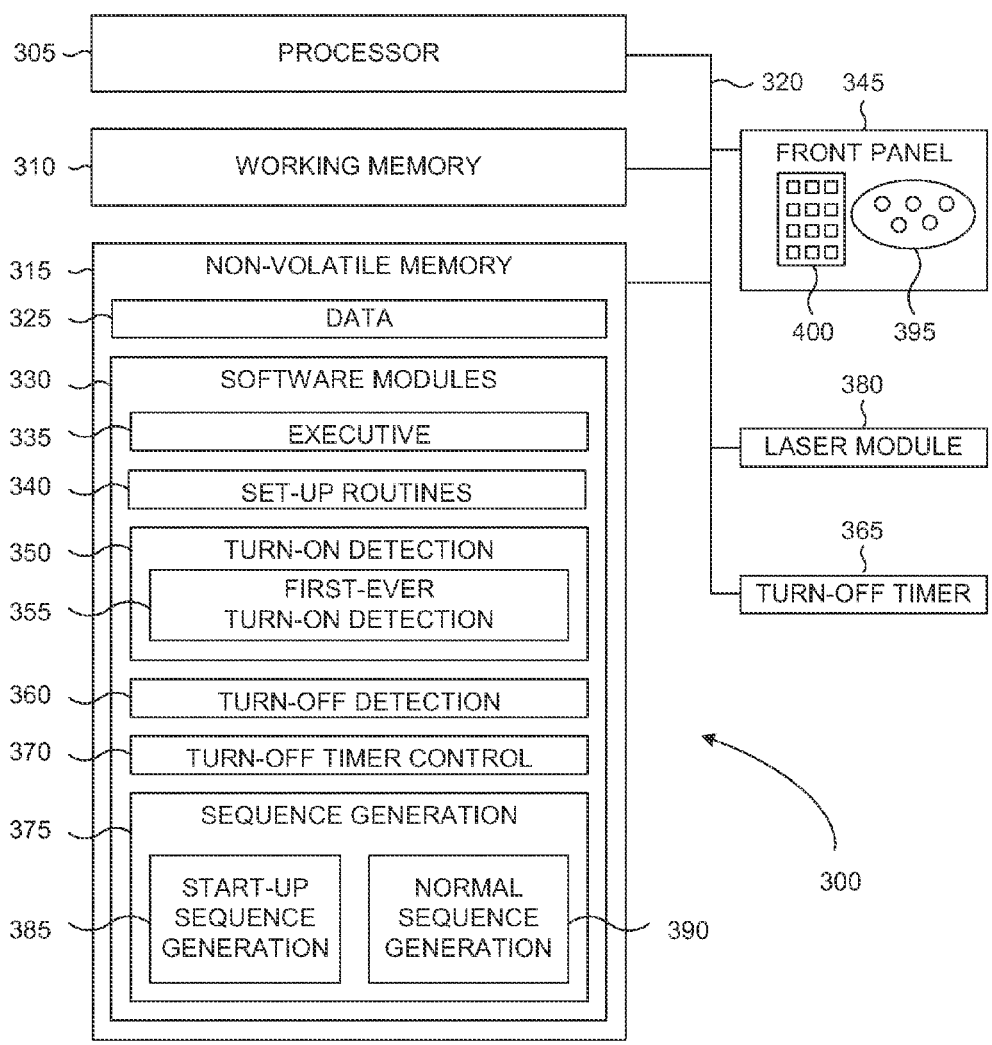
FIG. 9 is a block diagram of a computing device that may control a startup sequence for a medical laser.

One embodiment of a controlling device that may implement the method of the present invention is described in FIG. 9, which illustrates in block diagram form a computing device that may control operation of a medical laser. In particular, the controlling device may operate to perform, in addition to other functions, control of a startup sequence for the laser according for example to the method described supra relative to FIG. 8, the startup sequences being exemplified supra relative to FIGS. 6 and 7.

The schematic embodiment of the controlling device (i.e., controller 300) may comprise a processor 305 adapted to execute software instructions, working memory 310, and non-volatile memory 315, the aforementioned elements being interconnected by and intercommunicating through a system bus 320. The non-volatile memory 315 (e.g., flash memory) may include a portion for storage of data 325 and a portion for storage of software modules 330 that may control operation of the controller 300. The software modules may include, among other things, an executive module 335 adapted to cause the processor 305 to perform overall scheduling and control of tasks, set-up routines 340 that may be adapted to cause the processor 305 to, for example, respond to a change in state of an on/off switch, turn on indicators 395 on a front panel 345, control a cooling fan (not shown), respond to operator input from a keypad 400 and the like. The collection of software modules 330 may, further, comprise a turn-on detection module 350 that may be adapted to cause the processor 305 to detect a turn-on event (cf. step 205 in FIG. 8). The turn-on detection module 350 may include a first-ever turn-on detection module 355 that may be adapted to cause the processor 305 to detect a first-ever turn-on event (cf. step 210 in FIG. 8). A turn-off detection module 360 may be included as one of the software modules 330, the turn-off detection module 360 being adapted to cause the processor 305 to detect a turn-off event (cf. step 230 in FIG. 8).

The controller 300 may comprise a turn-off timer 365 that may be started (cf. step 235 in FIG. 8), stopped or interrogated by the processor 305 according to software instructions in a turn-off timer control module 370.

The collection of software modules 330, still further, may comprise a sequence generation module 375 that may cause the processor 305 to cause a laser module 380 to generate one of a startup sequence and a normal sequence according to instructions in a startup sequence generation module 385 and a normal sequence generation module 390 as described herein with regard to FIGS. 4, 6 and 7. The front panel 345, the laser module 380 and the turn-off timer 365 may also connect to the system bus 320 and may intercommunicate thereby with the processor 305.

One mode of operation of the controller 300 in FIG. 9 may comprise implementation of the flow diagram shown in FIG. 8 whereby temperature/power of a laser output can be increased gradually so that heating, melting, and/or evaporation of debris or moisture on (an) optical surface(s) of the laser occur relatively gently, gradually and/or controllably. Catastrophic burning may be thereby avoided with a result that fiber/optics of the medical laser are not damaged at all or are damaged to a lesser degree than might be the case with prior-art devices.

According to an aspect of the present invention, a medical handpiece includes a handpiece housing and a source of electromagnetic energy disposed within the handpiece housing and adapted for emitting electromagnetic energy from a distal end of the handpiece housing. An illumination source may be disposed within the handpiece housing for projecting light from the distal end of the handpiece housing onto a target surface. The illumination source may include a fiber optic bundle. A medication line may also be disposed within the handpiece housing for outputting medication through a distal end of the handpiece housing onto a target surface.

According to certain implementations, laser energy from a trunk fiber is output from a power or treatment fiber, and is directed, for example, into fluid (e.g., an air and/or water spray or an atomized distribution of fluid particles from a water connection and/or a spray connection near an output end of a handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

By way of the disclosure herein, a laser assembly has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of treatment radiation and/or of the fluid from the fluid output or outputs.

The present invention has applicability in the field of radiation outputting systems and processes in general, such as devices (e.g., LEDs, headlamps, etc.) that emit, reflect or channel radiation. Corresponding or related structure and methods described in the following patents assigned to Biolase Technology, Inc. disclosed or referenced herein and/or in any and all co-pending, abandoned or patented application(s) naming any of the named inventor(s) or assignee(s) of this disclosure and invention, are incorporated herein by reference in their entireties, wherein such incorporation includes corresponding or related structure (and modifications thereof) in the following patents which may be, in whole or in part, (i) operable and/or constructed with, (ii) modified by one skilled in the art to be operable and/or constructed with, and/or (iii) implemented/made/used with or in combination with, any part(s) of the present invention according to this disclosure, that of the patents or below applications, application and references cited therein, and the knowledge and judgment of one skilled in the art.

Such patents include, but are not limited to U.S. Pat. No. 7,970,030 entitled Dual pulse-width medical laser with presets; U.S. Pat. No. 7,970,027 entitled Electromagnetic energy distributions for electromagnetically induced mechanical cutting; U.S. Pat. No. 7,967,017 entitled Methods for treating eye conditions; U.S. Pat. No. 7,957,440 entitled Dual pulse-width medical laser; U.S. Pat. No. 7,942,667 entitled Electromagnetic radiation emitting toothbrush and dentifrice system; U.S. Pat. No. 7,909,040 entitled Methods for treating eye conditions; U.S. Pat. No. 7,891,363 entitled Methods for treating eye conditions; U.S. Pat. No. 7,878,204 entitled Methods for treating hyperopia and presbyopia via laser tunneling; U.S. Pat. No. 7,867,223 entitled Methods for treating hyperopia and presbyopia via laser tunneling; U.S. Pat. No. 7,817,687 entitled Electromagnetic energy distributions for electromagnetically induced mechanical cutting; U.S. Pat. No. 7,815,630 entitled Target-close electromagnetic energy emitting device; U.S. Pat. No. 7,751,895 entitled Tissue treatment device and method; U.S. Pat. No. 7,702,196 entitled Modified-output fiber optic tips; U.S. Pat. No. 7,697,814 entitled Radiation emitting apparatus with spatially controllable output energy distributions; U.S. Pat. No. 7,696,466 entitled Electromagnetic energy distributions for electromagnetically induced mechanical cutting; U.S. Pat. No. 7,695,469 entitled Electromagnetic energy output system; U.S. Pat. No. 7,665,467 entitled Methods for treating eye conditions; U.S. Pat. No. 7,630,420 entitled Dual pulse-width medical laser; U.S. Pat. No. 7,620,290 entitled Modified-output fiber optic tips; U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device; U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20110192405 entitled Methods for treating eye conditions; App. Pub. 20110172650 entitled Methods for treating eye conditions; App. Pub. 20110165535 entitled Handpiece finger switch for actuation of handheld medical instrumentation; App. Pub. 20110151394 entitled Plaque toothtool and dentifrice system; App. Pub. 20110096802 entitled High power radiation source with active-media housing; App. Pub. 201100965.49 entitled High power radiation source with active-media housing; App. Pub. 20110129789 entitled Drill and flavored fluid particles combination; App. Pub. 20110082526 entitled Target-close electromagnetic energy emitting device; App. Pub. 20110059417 entitled Fluid and pulsed energy output system; App. Pub. 20110032958 entitled Electromagnetic energy distributions for electromagnetically induced mechanical cutting; App. Pub. 20100233645 entitled Efficient laser and fluid conditioning and cutting system; App. Pub. 20100185188 entitled Electromagnetically induced treatment devices and methods; App. Pub. 20100167228 entitled Electromagnetic radiation emitting toothbrush and dentifrice system; App. Pub. 20100151407 entitled Device having activated textured surfaces for treating oral tissue; App. Pub. 20100151406 entitled Fluid conditioning system; App. Pub. 20100145323 entitled Electromagnetic energy output system; App. Pub. 20100145323 entitled Electromagnetic energy output system; App. Pub. 20100137852 entitled Non-contact handpiece for laser tissue cutting; App. Pub. 20100100086 entitled Satellite-platformed electromagnetic energy treatment device; App. Pub. 20100125291 entitled Drill and flavored fluid particles combination; App. Pub. 20100086892 entitled Modified-output fiber optic tips; App. Pub. 20100042082 entitled Methods and devices for treating presbyopia; App. Pub. 20090298004 entitled Tunnelling probe; App. Pub. 20090281531 entitled Interventional and therapeutic electromagnetic energy systems; App. Pub. 20090225060 entitled Wrist-mounted laser with animated, page-based graphical user-interface; App. Pub. 20090143775 entitled Medical laser having controlled-temperature and sterilized fluid output; App. Pub. 20090141752 entitled Dual pulse-width medical laser with presets; App. Pub. 20090105707 entitled Drill and flavored fluid particles combination; App. Pub. 20090104580 entitled Fluid and pulsed energy output system; App. Pub. 20090076490 entitled Fiber tip fluid output device; App. Pub. 20090075779 entitled Probes and biofluids for treating and removing deposits from tissue surfaces; App. Pub. 20090067189 entitled Contra-angle rotating handpiece having tactile-feedback tip ferrule; App. Pub. 20090062779 entitled Methods for treating eye conditions with low-level light therapy; App. Pub. 20090056044 entitled Electromagnetic radiation emitting toothbrush and dentifrice system; App. Pub. 20090043364 entitled Electromagnetic energy distributions for electromagnetically induced mechanical cutting; App. Pub. 20090042171 entitled Fluid controllable laser endodontic cleaning and disinfecting system; WO 2010/051579, entitled Surface structure modification; App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20090225060 entitled Wrist-mounted laser with animated, page-based graphical user-interface; App. Pub. 20090143775 entitled Medical laser having controlled-temperature and sterilized fluid output; App. Pub. 20090141752 entitled Dual pulse-width medical laser with presets; App. Pub. 20090105707 entitled Drill and flavored fluid particles combination; App. Pub. 20090104580 entitled Fluid and pulsed energy output system; App. Pub. 20090076490 entitled Fiber tip fluid output device; App. Pub. 20090075229 entitled Probes and biofluids for treating and removing deposits from tissue surfaces; App. Pub. 20090067189 entitled Contra-angle rotating handpiece having tactile-feedback tip ferrule; App. Pub. 20090062779 entitled Methods for treating eye conditions with low-level light therapy; App. Pub. 20090056044 entitled Electromagnetic radiation emitting toothbrush and dentifrice system; App. Pub. 20090043364 entitled Electromagnetic energy distributions for electromagnetically induced mechanical cutting; App. Pub. 20090042171 entitled Fluid controllable laser endodontic cleaning and disinfecting system; App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080317429 entitled Modified-output fiber optic tips; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled Multiple fiber-type tissue treatment device and related method; App. Pub. 20080219629 entitled Modified-output fiber optic tips; App. Pub. 20080212624 entitled Dual pulse-width medical laser; App. Pub. 20080203280 entitled Target-close electromagnetic energy emitting device; App. Pub. 20080181278 entitled Electromagnetic energy output system; App. Pub. 20080181261 entitled Electromagnetic energy output system; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080138764 entitled Fluid and laser system; App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080069172 entitled Electromagnetic energy distributions for electromagnetically induced mechanical cutting; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070128576 entitled Output attachments coded for use with electromagnetic-energy procedural device; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070016176 entitled Laser handpiece architecture and methods; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142745 entitled Dual pulse-width medical laser with presets; App. Pub. 20060142744 entitled Identification connector for a medical laser handpiece; App. Pub. 20060142743 entitled Medical laser having controlled-temperature and sterilized fluid output; App. Pub. 20060126680 entitled Dual pulse-width medical laser; App. Pub. 20060099548 entitled Caries detection using timing differentials between excitation and return pulses; App. Pub. 20060083466 entitled Fiber tip detector apparatus and related methods; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20050256517 entitled Electromagnetically induced treatment devices and methods; App. Pub. 20050256516 entitled Illumination device and related methods; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding applications are incorporated herein by reference in their entireties. Although the disclosure herein refers to certain illustrated embodiments, it is to be understood that these embodiments have been presented by way of example rather than limitation. For example, any of the radiation outputs (e.g., laser outputs), any of the fluid outputs (e.g., water outputs), and any conditioning agents, particles, agents, etc., and particulars or features thereof or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. A method of activating a medical laser, the method comprising:
   detecting a turn-on event;
   determining if the turn-on event has occurred after an extended period of non-use of the medical laser, wherein the extended period of non-use causes debris or moisture to form on one or more optical components of the medical laser, wherein the determining if the turn-on event has occurred after the extended period of non-use includes:
   determining if the turn-on event is a first-time-ever turn-on event;
   generating a ramp-up sequence of pulsed energy output of the medical laser conditional upon determining that the turn-on event is a first-time-ever turn-on event;
   determining if a turn-off timer has expired conditional upon determining that the turn-on event is not a first-time-ever turn-on event, the turn-off timer being a timer that begins to run when the medical laser is turned off and that expires after a period of time;
   generating a ramp-up sequence of pulsed energy output of the medical laser conditional upon determining that the turn-off timer has expired;
   initiating a normal startup sequence of pulsed energy output of the medical laser, without using the ramp-up sequence of pulsed energy output, conditional upon determining that the turn-off timer has not expired.

2. The method as set forth in claim 1, wherein the determining if the turn-on event has occurred after the extended period of non-use is performed in response to the detecting of the turn-on event.

3. The method as set forth in claim 1, further comprising:
   detecting a turn-off event; and
   starting the turn-off timer.

4. The method as set forth in claim 3, wherein the starting is performed in response to the detecting of the turn-off event.

5. The method of claim 1, wherein the one or more optical components of the medical laser includes a fiber tip.

6. The method of claim 1, wherein the ramp up sequence of pulsed energy output causes the moisture or debris to be heated, melted, or evaporated in a controllable manner or a gradual manner.

7. The method of claim 6, further comprising: heating, melting, or evaporating the moisture or debris in the controllable or gradual manner, wherein the controllable manner or the gradual manner prevents damage to the medical laser.

8. The method of claim 1, wherein the period of time is within a range of 30 seconds to 10 minutes.

9. The method of claim 1, further comprising:
   detecting the first-time-ever turn-on event, wherein the first-time-ever turn-on event includes turning on the medical laser that has never before been operated.

10. The method of claim 1, further comprising:
    detecting the first- time-ever turn-on event, wherein the first-time-ever turn-on event includes turning on the medical laser for a first time after the medical laser has been out of service due to maintenance.

11. The method of claim 1, wherein the ramp-up sequence of pulsed energy output includes a plurality of pulses including a first pulse and at least one other pulse, each of the pulses having a power level less than a set power level for the medical laser.

12. The method of claim 11, further comprising:
    wherein the normal startup sequence of pulsed energy output includes a plurality of pulses having a power equal to the set power level.

13. The method of claim 11, wherein the power level of the plurality of pulses is approximately at $1/10$th of the set power level.

14. The method of claim 11, wherein each pulse occurring after the first pulse has a power level that is not greater than a power level of a preceding pulse in the ramp-up sequence of pulsed energy output.

15. The method of claim 11, wherein each pulse occurring after the first pulse has a power level that is not less than a power level of a preceding pulse in the ramp-up sequence.

16. The method of claim 15, wherein each pulse occurring after the first pulse has the power level that is greater than the power level of the preceding pulse in the ramp-up sequence of pulsed energy output.

* * * * *